(12) United States Patent
Perlo et al.

(10) Patent No.: US 7,086,637 B2
(45) Date of Patent: Aug. 8, 2006

(54) RADIOFREQUENCY-CONTROLLED DEVICE FOR RELEASE/SAMPLING OF SUBSTANCES

(75) Inventors: Piero Perlo, Sommariva Bosco (IT); Anatoli Zvezdine, Orbassano (IT); Valentina Grasso, Carignano (IT); Federica Valerio, Orbassano (IT); Vito Guido Lambertini, Giaveno (IT); Daniele Pullini, Orbassano (IT); Nello Li Pira, Fossano (IT); Piermario Repetto, Turin (IT); Gianfranco Innocenti, Rivalta (IT)

(73) Assignee: C.R.F. Societa Consortile per Azioni, Orbassamp (IT)

( * ) Notice: Subject to any disclaimer, the term of this patent is extended or adjusted under 35 U.S.C. 154(b) by 85 days.

(21) Appl. No.: 10/853,112

(22) Filed: May 26, 2004

(65) Prior Publication Data
US 2004/0238769 A1    Dec. 2, 2004

(30) Foreign Application Priority Data
May 27, 2003   (IT)   ......................... TO2003A0390

(51) Int. Cl.
*F16K 31/02*    (2006.01)

(52) U.S. Cl. .................................................. 251/129.04

(58) Field of Classification Search ........... 251/129.04
See application file for complete search history.

(56) References Cited

U.S. PATENT DOCUMENTS

| | | |
|---|---|---|
| 5,170,801 A | 12/1992 | Casper et al. |
| 5,405,614 A | 4/1995 | D-Angelo et al. |
| 2001/0044620 A1 | 11/2001 | Krulevitch et al. |
| 2002/0013555 A1 | 1/2002 | Seward |

FOREIGN PATENT DOCUMENTS

| | | |
|---|---|---|
| WO | WO 98/52640 | 11/1998 |
| WO | WO 02/30264 A2 | 4/2002 |

*Primary Examiner*—J. Casimer Jacyna
(74) *Attorney, Agent, or Firm*—Sughrue Mion, PLLC

(57) ABSTRACT

The present invention relates to a miniaturized device controlled by electromagnetic signals in the radiofrequency range for controlled release of substances or for controlled sampling of specimens, comprising a reservoir, and a closing system associated to said reservoir, where said closing system is constituted by a valve structure, closing-opening of which is controlled by the electromagnetic signal in the radiofrequency range.

9 Claims, 2 Drawing Sheets

RADIOFREQUENCY-CONTROLLED DEVICE FOR RELEASE/SAMPLING OF SUBSTANCES

BACKGROUND OF THE INVENTION

The present invention relates to a miniaturized device controlled by electromagnetic signals in the radiofrequency range for the controlled release or sampling of substances or specimens, which, thanks to its small dimensions, is suited to being integrated in a capsule for medical, industrial or environmental uses, for example, for release of a drug along the gastrointestinal tract of a living organism after ingestion. In particular, the device according to the present invention comprises a reservoir and a valve structure associated to said reservoir, the functions of opening and closing of which are controlled by an electromagnetic signal in the radiofrequency range.

SUMMARY OF THE INVENTION

A device controlled by electromagnetic signals in the radiofrequency range capable of controlling the release of a substance is described in the international patent application WO 02/30264. The aforesaid device has: a support having a plurality of reservoirs containing the substance to be released; a closing system for each reservoir; and a source of energy capable of receiving an electromagnetic signal in the radiofrequency range and transmitting said signal to the closing system so as to bring about opening thereof with subsequent release of the substance. The closing system of the reservoir is substantially constituted by a coating capable of disintegrating or varying its own porosity to such an extent as to enable release of the substance contained in the reservoir itself. The electromagnetic signal received by the energy source is transduced into a variation of electric potential, which, when applied to an anode/cathode pair, where the anode is constituted by the closing system of the reservoir, brings about disintegration or variation in porosity of the anode, with consequent release of the substance contained in the reservoir into the environment.

The purpose of the present invention is to provide a device controlled by electromagnetic signals in the radiofrequency range for controlled release/sampling of substances or specimens, said device being improved, for example, as regards the structure itself of the device, which is simplified, and/or as regards other functional aspects and aspects of use.

The purpose of the present invention is to provide a miniaturized device controlled by an electromagnetic signal in the radiofrequency range for controlled release or sampling of substances or specimens such as to implement the aforesaid improvements.

According to the invention, said purpose is achieved thanks to the solution recalled specifically in the ensuing claims, which are to be understood as forming an integral part of the present description.

In the currently preferred embodiment, the invention relates to a valve of general use, which can, in particular, be applied to a device for controlled release or sampling of substances or specimens, comprising: a communication module, capable of detecting and responding to electromagnetic signals in the radiofrequency range; a battery; a reservoir; and a valve structure associated to said reservoir, the closing-opening of which is controlled by the electromagnetic signal through actuation of the battery.

An even more preferred embodiment of the present invention relates to a device comprising a reservoir and a valve structure associated to said reservoir, where the valve structure is constituted by material sensitive to radiofrequencies, and in particular to circularly polarized radiofrequencies, in such a way that the functions of closing and opening of said valve structure are controlled by the electromagnetic signal acting directly on said material.

BRIEF DESCRIPTION OF THE DRAWINGS

Further characteristics and advantages of the device according to the present invention will emerge clearly evident in the course of the ensuing detailed description, provided purely by way of non-limiting example, with reference to the annexed drawings, in which.

DETAILED DESCRIPTION OF THE INVENTION

Figure 1A:
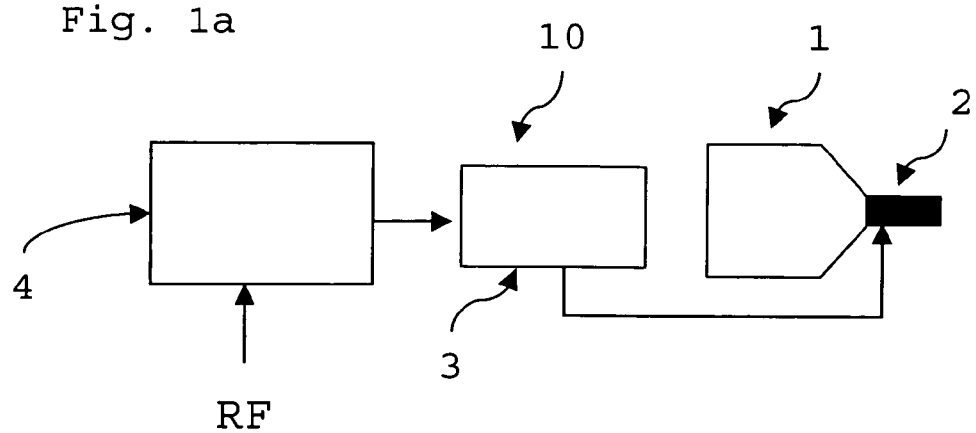
FIG. 1a represents a device for controlled release/sampling of a substance with the valve in the closed position.

With reference to FIG. 1, the device designated, as a whole, by the reference number 10 comprises: a communication module 4 capable of detecting and responding to an electromagnetic signal in the radiofrequency range RF; a battery 3; and a reservoir 1, associated to which is a valve structure 2.

The valve structure 2 has parts of wall 2a and 2b that jointly define a flow pipe 5, through which there can flow the substance contained in the reservoir 1.

Figure 1B:
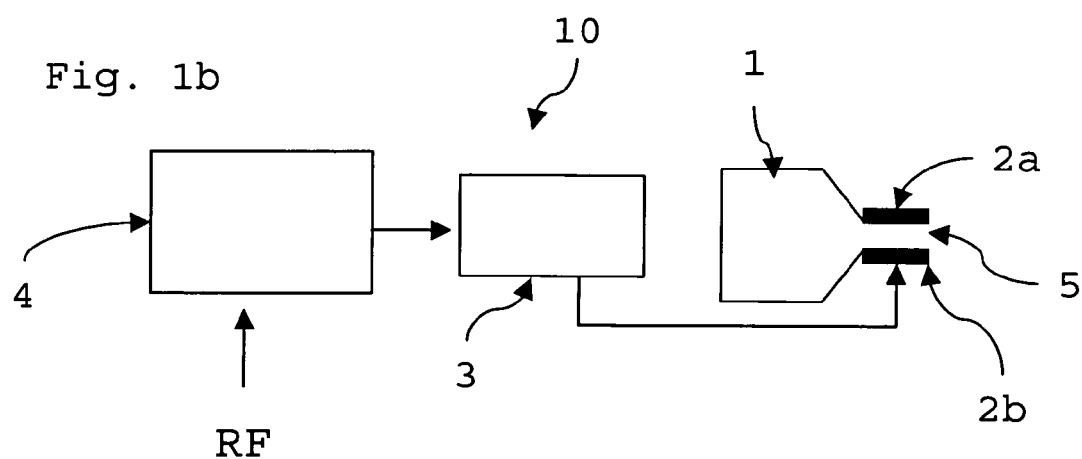
FIG. 1b represents a device for controlled release/sampling of a substance with the valve in the open position.

The material that constitutes said parts of wall 2a and 2b is a material sensitive to heat, such as, for example, a shape-memory alloy, hence capable of modifying its own conformation according to the temperature. The application of a current, and hence of heat, to said valve structure 2 modifies selectively the position of said parts of wall 2a and 2b so as to render the flow pipe 5 selectively closed (FIG. 1a) or pervious (FIG. 1b).

The communication module 4, which operates, for example, according to a protocol such as IEEE 802.11, GSM, Bluetooth, and ZigBee, is integrated with a control board or else with an electronic regulation system, which acts on the battery 3. The communication module 4 is able to detect an electromagnetic signal in the radiofrequency range in the ISM (Industrial Scientific and Medical frequency) bands, which, for Europe, is located at 430 MHz and, for the United States, at 900 MHz.

The electromagnetic signal detected by the communication module 4 acts, via the control board or the electronic regulation system, on the battery 3, which induces—by the Joule effect—heating of the valve structure 2, regulating closing/opening of the flow pipe 5 and consequently of the reservoir 1, with corresponding release or sampling of the substance/specimen of interest.

Interruption of the electromagnetic signal brings the valve structure 2 back again into its initial condition, interrupting its operation, which may however be resumed with the emission of another electromagnetic signal.

In the embodiment illustrated in FIG. 2, the device 20 controlled by an electromagnetic signal in the radiofrequency range for release/sampling of a substance/specimen comprises a reservoir 1, associated to which is a valve structure 2, having structural parts altogether similar to the ones already illustrated with reference to FIG. 1.

In this second embodiment, it is the valve structure 2 as a whole that is sensitive to electromagnetic signals in the radiofrequency range; said signals are capable of modifying the physical characteristics of the material constituting at least one of the parts of wall 2a and 2b, with corresponding variation of the relative position of the two parts of wall 2a and 2b so as to render the flow pipe 5 selectively closed or pervious.

Figure 2:
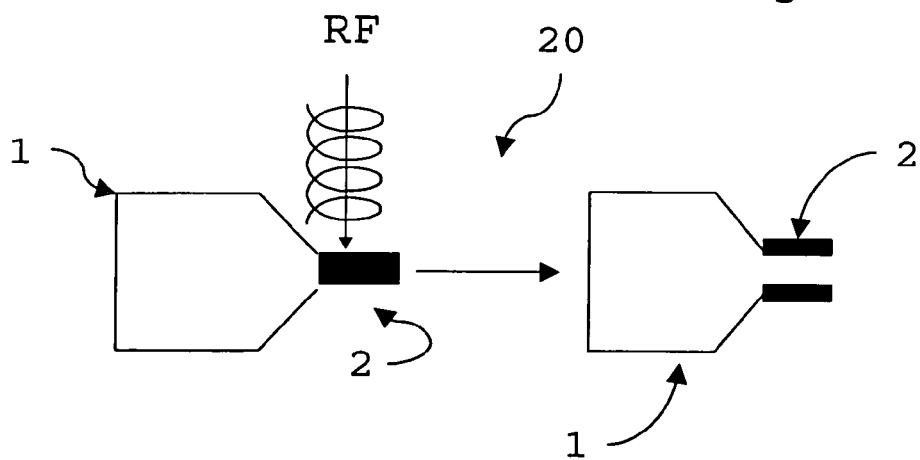
FIG. 2 represents a second embodiment of device for controlled release/sampling of a substance according to the present invention.

The device 20 illustrated in FIG. 2 is further simplified with respect to the device 10 of FIG. 1, for operation of which a communication module and a battery are envisaged. The embodiment illustrated in FIG. 2 does not require for its operation said additional elements.

The closing system of the device 20 comprises substantially a valve structure 2, possibly co-operating with further mechanical elements.

The valve structure 2 of the device 20 envisages the use of two materials with different physical properties constituting each of the two parts of wall 2a and 2b.

The part of wall 2a may for example be constituted by a material sensitive to radiofrequencies and, in particular, to a field of circularly polarized radiation, and hence subject to variations in its physical properties, and in particular magnetic properties, when it is subjected to an electromagnetic signal in the radiofrequency range. An example of a material of this type is constituted by a soft magnetic material; for instance, gadolinium iron garnet (GdIG), having the composition $Gd_3Fe_5O_{12}$, may be cited. A soft magnetic material of this sort presents weak magnetic properties and has a compensation temperature at which said magnetic properties are lost.

The part of wall 2b, instead, can be made of course of a permanently magnetic or magnetized material, for example, $NdFe_{14}B$.

When the part of wall 2a is irradiated by circularly polarized electromagnetic waves in the radiofrequency range, a state of magnetization is induced in the soft magnetic material that is repulsive with respect to the state of magnetization of the permanent magnet constituting the part of wall 2b, with consequent opening of the flow pipe 5 and release of the substance contained in the reservoir 1.

Figure 3:
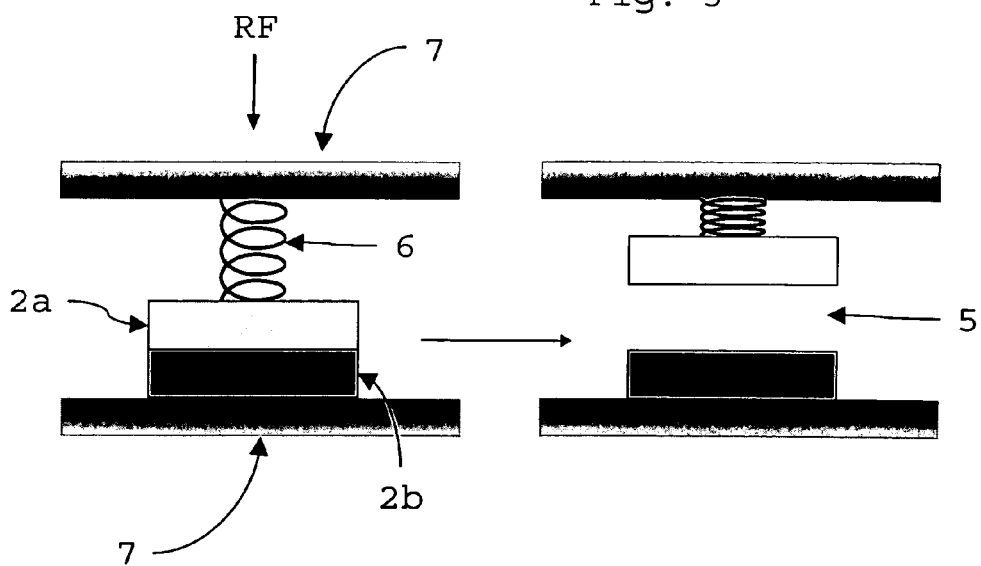
FIGS. 3 and 4 illustrate two examples of embodiment of the closing system of the device of FIG. 2.
Figure 4:
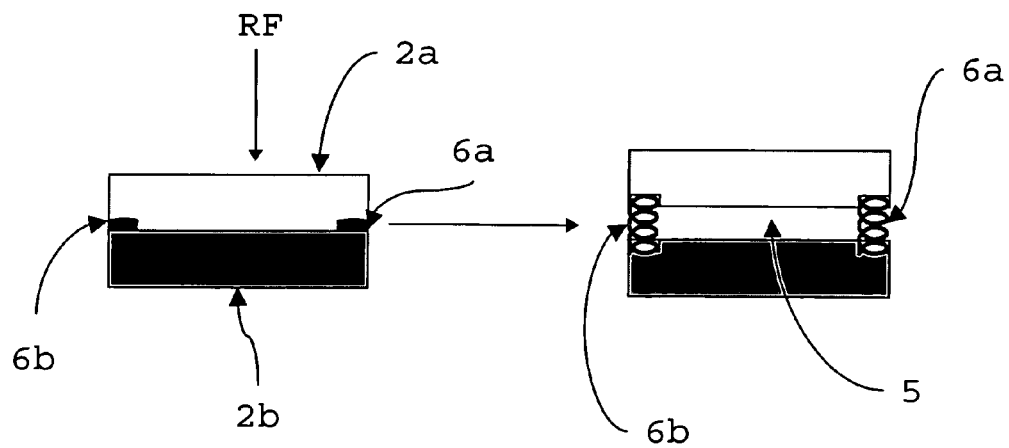

FIGS. 3 and 4 represent two further particular embodiments of the closing system of the device 20.

The closing system in the configuration of FIG. 3 envisages interposition of a mechanical element in the form of one or more springs 6 between one of the two parts of wall 2a or 2b of the valve structure 2 and a surface 7 of a container (not illustrated) within which the device 20 is housed (for example, the internal wall of a capsule).

The spring 6 co-operates with the valve structure 2, facilitating closing thereof in conditions of absence of any electromagnetic signal.

When the soft magnetic material constituting the part of wall 2a is impinged upon by electromagnetic waves in the radiofrequency range, the repulsive magnetic force that said material acquires in regard to the material constituting the part of wall 2b overcomes the elastic force exerted by the spring 6, leading to the variation in position of said parts of wall 2a and 2b, i.e., to opening of the flow pipe 5 and to release or sampling of the substance/specimen.

When the electromagnetic signal ceases, the soft magnetic material looses its magnetization, and the elastic force of the spring 6 brings the two parts of wall 2a and 2b back again into contact with one another, so choking the flow pipe 5.

In the second embodiment represented in FIG. 4, the closing system of the device 20 envisages the interposition of one or more mechanical elements, for example, in the form of springs 6a and 6b co-operating with the two parts of wall 2a and 2b.

The two parts of wall 2a and 2b are constituted by materials with different magnetic properties. Reference may be made to what has been described previously in relation to the device 20 of FIG. 2 as regards the materials and the corresponding magnetic properties.

The springs 6a and 6b maintain the two parts of wall 2a and 2b separated from one another on account of their elastic force, with consequent perviousness of the flow pipe 5 and release of the substance contained in the reservoir.

Application of an electromagnetic signal in the radiofrequency range varies the condition of magnetization of the material constituting, for example, the part of wall 2a by inducing an attractive magnetic force between the two parts of wall 2a and 2b in such a way as to overcome the elastic force of the springs 6a and 6b and choke the flow pipe 5.

The process in both of the configurations is reversible: when the electromagnetic signal is interrupted, the soft magnetic material returns to its initial condition, and the valve structure 2 closes or opens.

The possibility of controlling opening or closing of the valve structure 2 of the device 20 by acting directly on the material of which the parts of wall are made via direct electromagnetic signals in the radiofrequency range enables elimination of the battery and the communication module, with consequent further miniaturization of the device.

Of course, without prejudice to the principle of the invention, the details of construction and the embodiments may vary with respect to what is described and illustrated herein, without thereby departing from the scope of the present invention.

What is claimed is:

1. A valve device controlled by an electromagnetic signal in the radiofrequency range for general use and in particular for release/sampling of a substance/specimen, said device comprising:
    a reservoir; and
    a closing system associated to said reservoir; said device being characterized in that said closing system comprises a valve structure and in that the functions of opening and closing of said valve structure are controlled by said electromagnetic signal in the radiofrequency range;
    wherein said valve structure is made up of at least one pair of parts of wall, which jointly define a flow pipe; and
    wherein at least one of said parts of wall is made of material sensitive to said electromagnetic signal in the radiofrequency range.

2. The device according to claim 1, wherein said material sensitive to said electromagnetic signal in the radiofrequency range varies at least one of its physical properties when it is irradiated by said electromagnetic signal in the radiofrequency range.

3. The device according to claim 2, wherein said physical property modified by said electromagnetic signal in the radiofrequency range is magnetism.

4. The device according to claim 1, wherein said material sensitive to said electromagnetic signal in the radiofrequency range is a soft magnetic material having a temperature of compensation at which it looses its magnetic properties.

5. The device according to claim 1, wherein said other part of wall is made of a permanently magnetic or magnetized material.

6. The device according to claim 4, wherein said soft magnetic material is $Gd_3Fe_5O_{12}$.

7. The device according to claim 5, wherein said permanently magnetized material is $NdFe_{14}B$.

8. A valve device controlled by an electromagnetic signal in the radiofrequency range for general use and in particular for release/sampling of a substance/specimen, said device comprising:
  a reservoir; and
  a closing system associated to said reservoir; said device being characterized in that said closing system comprises a valve structure and in that the functions of opening and closing of said valve structure are controlled by said electromagnetic signal in the radiofrequency range;
  wherein said device is contained inside a container;
  wherein said valve structure is made up of at least one pair of parts of wall, which jointly define a flow pipe; and
  wherein at least one spring is set between an external surface of said container and at least one of said parts of wall.

9. A valve device controlled by an electromagnetic signal in the radiofrequency range for general use and in particular for release/sampling of a substance/specimen, said device comprising:
  a reservoir; and
  a closing system associated to said reservoir; said device being characterized in that said closing system comprises a valve structure and in that the functions of opening and closing of said valve structure are controlled by said electromagnetic signal in the radiofrequency range;
  wherein said device is contained inside a container;
  wherein said valve structure is made up of at least one pair of parts of wall, which jointly define a flow pipe; and
  wherein at least one spring is set between an said two parts of wall.

* * * * *